US009940952B2

(12) United States Patent
Biskeborn et al.

(10) Patent No.: US 9,940,952 B2
(45) Date of Patent: Apr. 10, 2018

(54) ABRASION TEST METHODS AND DEVICES

(71) Applicant: International Business Machines Corporation, Armonk, NY (US)

(72) Inventors: Robert G. Biskeborn, Hollister, CA (US); Jason Liang, Campbell, CA (US); Calvin S. Lo, Saratoga, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/860,551

(22) Filed: Sep. 21, 2015

(65) Prior Publication Data
US 2016/0033381 A1 Feb. 4, 2016

Related U.S. Application Data

(62) Division of application No. 13/358,415, filed on Jan. 25, 2012, now Pat. No. 9,293,152.

(51) Int. Cl.
*G01N 19/02* (2006.01)
*G11B 5/255* (2006.01)
*G11B 5/187* (2006.01)
*G01N 3/56* (2006.01)
*G11B 5/455* (2006.01)
*G11B 5/008* (2006.01)

(52) U.S. Cl.
CPC ............ *G11B 5/255* (2013.01); *G01N 3/56* (2013.01); *G11B 5/00821* (2013.01); *G11B 5/187* (2013.01); *G11B 5/455* (2013.01)

(58) Field of Classification Search
CPC ........................................................ G01N 3/56
USPC ................................................................ 73/7
See application file for complete search history.

(56) References Cited

U.S. PATENT DOCUMENTS

| 3,753,093 | A | * | 8/1973 | Gardner | G01N 3/56 |
| | | | | | 324/699 |
| 4,091,654 | A | | 5/1978 | Hurtig et al. | |
| 6,040,693 | A | * | 3/2000 | Sakai | G11B 5/00 |
| | | | | | 324/210 |
| 6,426,848 | B1 | | 7/2002 | Tamura et al. | |
| 6,515,833 | B1 | | 2/2003 | Shirai et al. | |
| 6,765,755 | B1 | * | 7/2004 | Jacquet | G11B 11/10547 |
| | | | | | 360/114.05 |
| 6,796,884 | B1 | | 9/2004 | Tran et al. | |
| 6,989,535 | B2 | | 1/2006 | Tani et al. | |

(Continued)

FOREIGN PATENT DOCUMENTS

| CN | 1643361 A | 7/2005 |
| JP | S62271215 A | 11/1987 |

(Continued)

OTHER PUBLICATIONS

Biskeborn et al., U.S. Appl. No. 14/860,535, filed Sep. 21, 2015.

(Continued)

*Primary Examiner* — Eric S McCall
*Assistant Examiner* — Mohammed E Keramet-Amircolai
(74) *Attorney, Agent, or Firm* — Zilka-Kotab, P.C.

(57) ABSTRACT

A method according to one embodiment includes measuring an initial coating thickness on a tape bearing surface of a module in a carrier, running a tape across the tape bearing surface, and at intervals, measuring a residual thickness of the coating.

20 Claims, 9 Drawing Sheets

(56) References Cited

U.S. PATENT DOCUMENTS

| | | | |
|---|---|---|---|
| 6,989,960 B2* | 1/2006 | Dugas | G11B 5/1276 29/603.15 |
| 7,013,705 B2* | 3/2006 | Wortmann | G01N 3/56 73/7 |
| 7,161,668 B2* | 1/2007 | Meeks | G01B 11/306 356/237.2 |
| 7,450,341 B2 | 11/2008 | Dugas et al. | |
| 7,509,833 B2* | 3/2009 | Biskeborn | G01N 3/56 73/7 |
| 7,630,086 B2* | 12/2009 | Oak | G01B 11/303 356/237.2 |
| 7,640,788 B2 | 1/2010 | Biskeborn et al. | |
| 7,714,995 B2* | 5/2010 | Meeks | G01B 11/0616 356/237.1 |
| 8,035,919 B2* | 10/2011 | Yari | G11B 5/102 360/110 |
| 8,621,910 B2 | 1/2014 | Biskeborn et al. | |
| 9,293,152 B2 | 3/2016 | Biskeborn et al. | |
| 9,659,581 B2 | 5/2017 | Biskeborn et al. | |
| 2002/0027744 A1 | 3/2002 | Sato | |
| 2003/0151853 A1 | 8/2003 | Fahimi et al. | |
| 2004/0072033 A1 | 4/2004 | Ide et al. | |
| 2004/0115454 A1 | 6/2004 | Lowery et al. | |
| 2004/0160604 A1 | 8/2004 | Meeks et al. | |
| 2005/0081599 A1 | 4/2005 | Wortmann et al. | |
| 2005/0084621 A1 | 4/2005 | Liu et al. | |
| 2005/0284207 A1 | 12/2005 | Biskeborn et al. | |
| 2007/0035877 A1 | 2/2007 | Maejima et al. | |
| 2007/0201165 A1* | 8/2007 | Kato | G11B 5/6064 360/234.5 |
| 2008/0144215 A1 | 6/2008 | Hsiao et al. | |
| 2008/0266711 A1 | 10/2008 | Nibarger et al. | |
| 2009/0052093 A1 | 2/2009 | Kawakita et al. | |
| 2009/0059413 A1 | 3/2009 | Escobar et al. | |
| 2009/0133468 A1 | 5/2009 | Biskeborn et al. | |
| 2009/0231743 A1 | 9/2009 | Kamimura et al. | |
| 2010/0053817 A1* | 3/2010 | Biskeborn | B82Y 10/00 360/313 |
| 2010/0149685 A1 | 6/2010 | Yari et al. | |
| 2010/0237345 A1* | 9/2010 | Nakazawa | G11B 5/00817 257/48 |
| 2010/0269565 A1* | 10/2010 | Biskeborn | G01N 3/56 73/7 |
| 2011/0043940 A1 | 2/2011 | Wagner et al. | |
| 2011/0102944 A1 | 5/2011 | Suzuki | |
| 2011/0256423 A1* | 10/2011 | Biskeborn | G11B 5/127 428/813 |
| 2013/0128371 A1* | 5/2013 | Brong | G11B 5/455 360/31 |
| 2013/0186172 A1 | 7/2013 | Biskeborn et al. | |
| 2014/0059842 A1 | 3/2014 | Biskeborn et al. | |
| 2015/0168283 A1 | 6/2015 | Biskeborn et al. | |
| 2016/0011092 A1 | 1/2016 | Biskeborn et al. | |
| 2016/0267926 A1 | 9/2016 | Li et al. | |
| 2017/0178671 A1 | 6/2017 | Biskeborn et al. | |

FOREIGN PATENT DOCUMENTS

| | | |
|---|---|---|
| JP | H08105723 A | 4/1996 |
| JP | 10255241 | 9/1998 |
| JP | 201158895 | 6/2001 |
| JP | 2005285252 A | 10/2005 |
| WO | 03056305 A1 | 7/2003 |

OTHER PUBLICATIONS

Restriction Requirement from U.S. Appl. No. 13/358,415, dated Feb. 14, 2014.

Final Office Action from U.S. Appl. No. 13/358,415, dated Oct. 24, 2014.

Final Office Action from U.S. Appl. No. 13/358,415, dated Feb. 25, 2015.

Biskeborn et al., U.S. Appl. No. 13/358,415, filed Jan. 25, 2012.

Biskeborn et al., U.S. Appl. No. 14/105,047, filed Dec. 12, 2013.

Ex Parte Quayle from U.S. Appl. No. 13/358,415, dated Jun. 18, 2015.

Non-Final Office Action from U.S. Appl. No. 13/358,415, dated Mar. 26, 2014.

Notice of Allowance from U.S. Appl. No. 13/358,415, dated Jul. 8, 2015.

Scott et al., "Corrosion and wear studies of uncoated and ultra-thin DLC coated magnetic tape-write heads and magnetic tapes", Wear, vol. 243, 2000, pp. 31-42.

Scott, "Micro/Nanoscale Differential Wear and Corrosion of Multiphase Materials Dissertation", 2001, pp. i-24.

Scott, "Micro/nano-scale differential wear of multiphase materials: pole tip recession in magnetic-tape heads", Wear, vol. 252, 2002, pp. 103-122.

Sourty et al., "Pole Tip Recession in Linear Recording Heads", IEEE Transactions on Magnetics, vol. 39, No. 3, May 2003, pp. 1859-1861.

Bhushan et al., "Friction and Wear of Particulate and ME Magnetic Tapes Sliding against a Mn—Zn Ferrite Head in a Linear Mode", IEEE Transactions on Magnetics, vol. 30, No. 6, Nov. 1994, pp. 4176-4178.

Notice of Allowance from U.S. Appl. No. 13/358,415, dated Dec. 4, 2015.

Notice of Allowance from U.S. Appl. No. 14/860,535, dated Jan. 19, 2017.

Statement of Relevance of Non-Translated Foreign Document JPS62271215.

Biskeborn et al., U.S. Appl. No. 15/446,976, filed Mar. 1, 2017.

Final Office Action from U.S. Appl. No. 14/860,535, dated Oct. 20, 2016.

Bhushan et al., "Friction and wear studies of various head materials and magnetic tapes in a linear mode accelerated test using a new nano-scratch wear measure technique," Wear, vol. 190, No. 1, Jan. 1995, pp. 1-15.

Gao, C., "Flying Stiction, Lubricant Pick-Up and Carbon-Overcoat Wear of Magnetic Heads", Journal of Tribology, vol. 121, Jan. 1999, pp. 97-101.

Non-Final Office Action from U.S. Appl. No. 14/860,535, dated Apr. 8, 2016.

Non-Final Office Action from U.S. Appl. No. 15/446,976, dated Aug. 10, 2017.

* cited by examiner

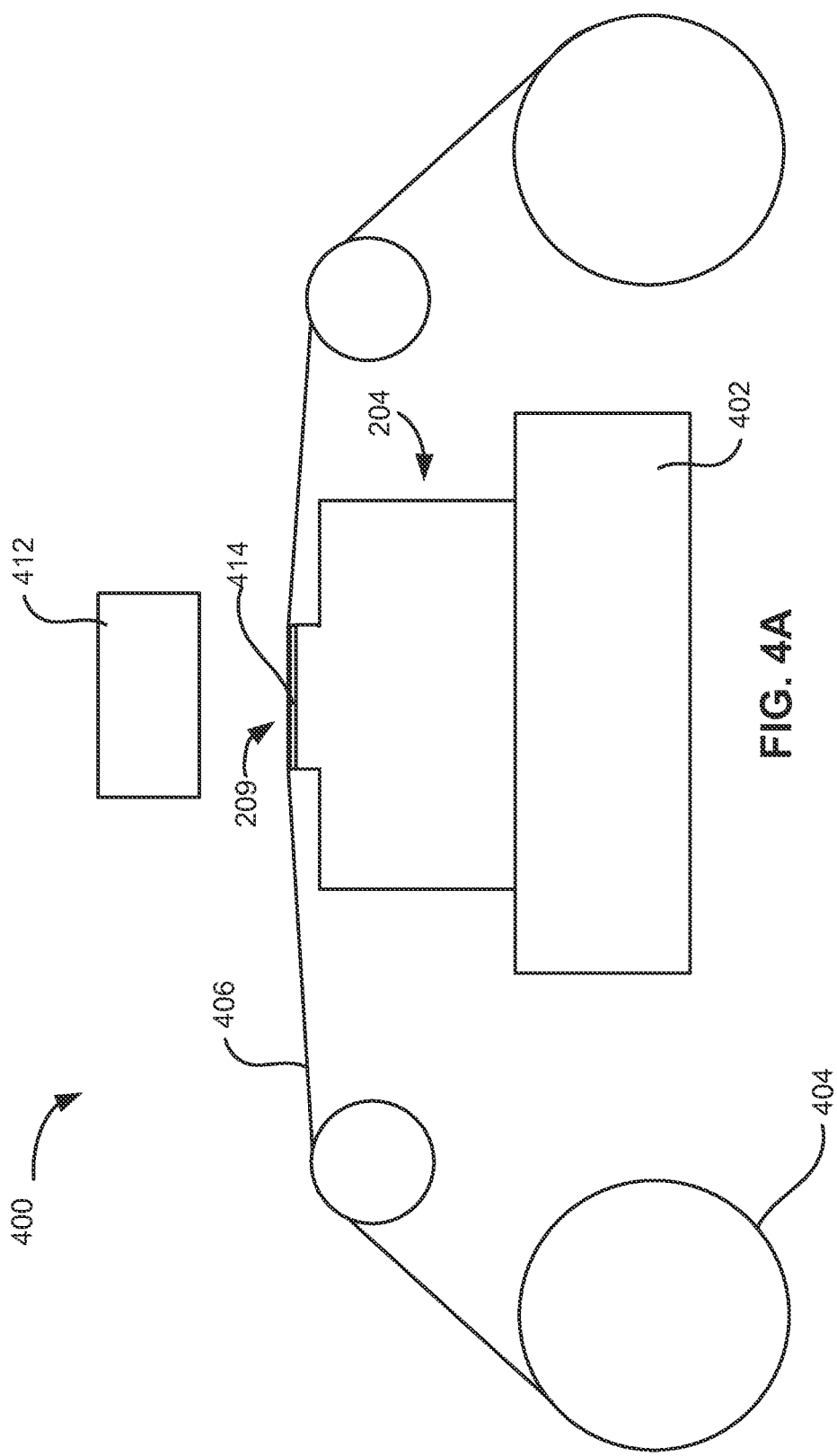

ABRASION TEST METHODS AND DEVICES

BACKGROUND

The present invention relates to media abrasivity testing, and more particularly, this invention relates to an improvement in the testing of media abrasivity and/or coating wear.

In magnetic storage systems, data is read from and written onto magnetic recording media utilizing magnetic transducers commonly. Data is written on the magnetic recording media by moving a magnetic recording transducer to a position over the media where the data is to be stored. The magnetic recording transducer then generates a magnetic field, which encodes the data into the magnetic media. Data is read from the media by similarly positioning the magnetic read transducer and then sensing the magnetic field of the magnetic media. Read and write operations may be independently synchronized with the movement of the media to ensure that the data can be read from and written to the desired location on the media.

An important and continuing goat in the data storage industry is that of increasing the density of data stored on a medium. For tape storage systems, that goal has led to increasing the track and linear bit density on recording tape, and decreasing the thickness of the magnetic tape medium. However, the development of small footprint, higher performance tape drive systems has created various problems in the design of a tape head assembly, as well as tapes, for use in such systems.

Media abrasivity is directly related to head wear, recession, and spacing loss. The current method employed by media vendors to gauge abrasivity involves methods which have been shown to not be representative of actual head wear, and a poor gauge of tape abrasivity.

SUMMARY

A method according to one embodiment includes measuring an initial coating thickness on a tape bearing surface of a module in a carrier, running a tape across the tape bearing surface, and at intervals, measuring a residual thickness of the coating.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 4A is a partial cross-sectional view of a tape head according to one embodiment.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of magnetic storage systems, as well as operation and/or component parts thereof.

In one general embodiment, a system includes a carrier for receiving a module; a transport mechanism for running a tape across a tape bearing surface of the module; and a measuring device for measuring an extent of wear of a coating on a tape bearing surface of the module.

In another general embodiment, a module includes a body having a tape bearing surface, the body having an approximate tape bearing surface profile and dimensions as a module of interest; and a coating on the tape bearing surface.

In another general embodiment, a method includes measuring an initial coating thickness on a tape bearing surface of a module in a carrier; running a tape across the tape bearing surface; and at intervals, measuring a residual thickness of the coating.

Figure 1:
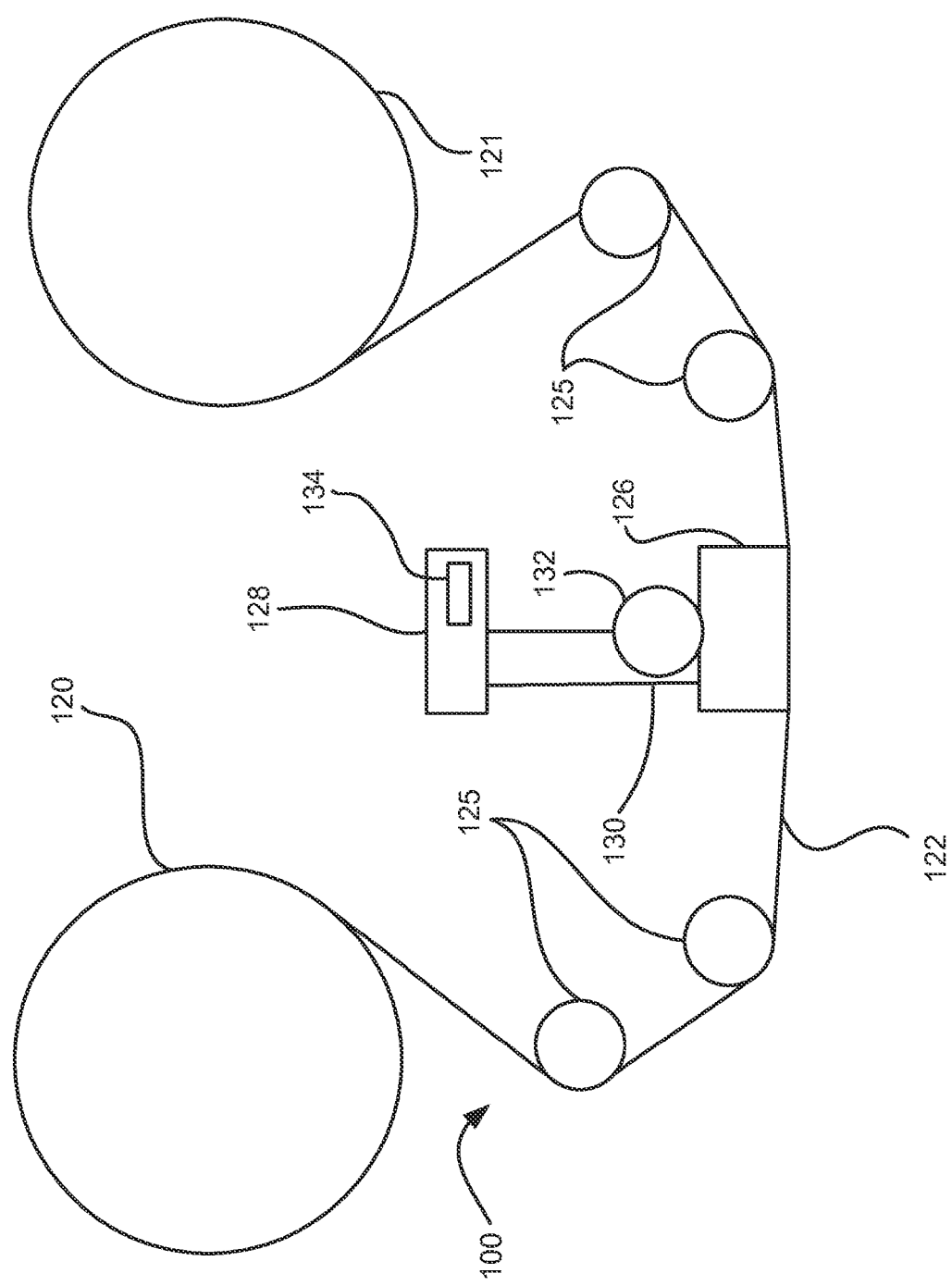
FIG. 1 is a schematic diagram of a simplified tape drive system according to one embodiment.

FIG. 1 illustrates a simplified tape drive 100 of a tape-based data storage system, which may be employed in the context of the present invention. While one specific implementation of a tape drive is shown in FIG. 1, it should be noted that the embodiments described herein may be implemented in the context of any type of tape drive system.

As shown, a tape supply cartridge 120 and a take-up reel 121 are provided to support a tape 122. One or more of the reels may form part of a removable cartridge and are not necessarily part of the system 100. The tape drive, such as that illustrated in FIG. 1, may further include drive motor(s) to drive the tape supply cartridge 120 and the take-up reel 121 to move the tape 122 over a tape head 126 of any type. Such head may include an array of readers, writers, or both.

Guides 125 guide the tape 122 across the tape head 126. Such tape head 126 is in turn coupled to a controller assembly 128 via a cable 130. The controller 128 typically controls head functions such as servo following, writing, reading, etc. The controller may operate under logic known in the art, as well as any logic disclosed herein. The cable 130 may include read/write circuits to transmit data to the head 126 to be recorded on the tape 122 and to receive data read by the head 126 from the tape 122. An actuator 132 controls position of the head 126 relative to the tape 122.

An interface 134 may also be provided for communication between the tape drive and a host (integral or external) to send and receive the data and for controlling the operation of the tape drive and communicating the status of the tape drive to the host, all as will be understood by those of skill in the art.

Figure 2:
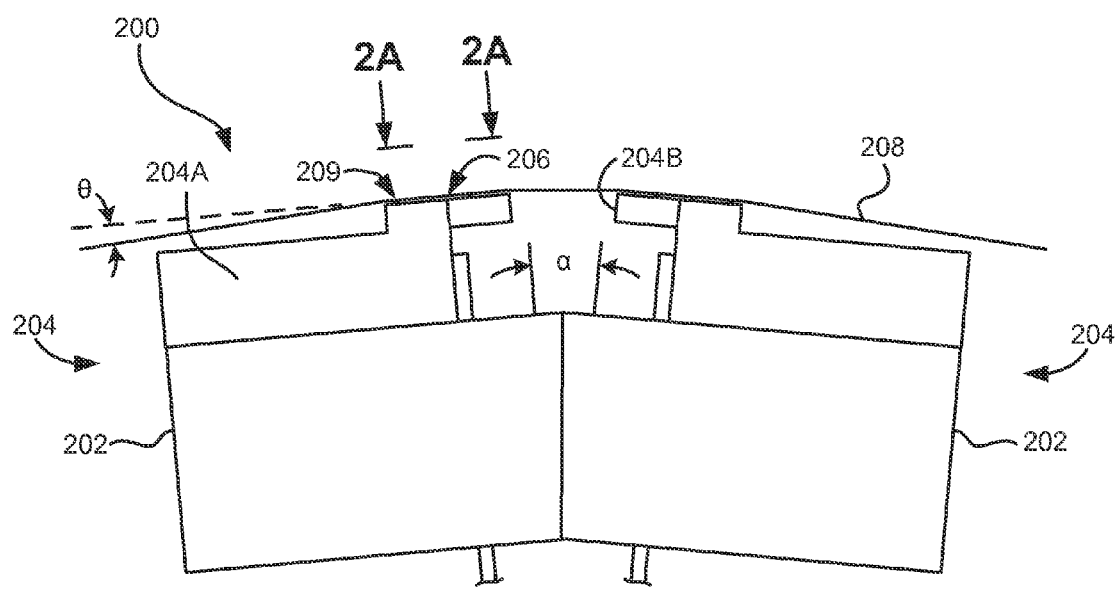
FIG. 2 illustrates a side view of a flat-lapped, bi-directional, two module magnetic tape head according to one embodiment.

By way of example, FIG. 2 illustrates a side view of a flat-lapped, bi-directional, two-module magnetic tape head 200 which may be implemented in the context of the present invention. As shown, the head includes a pair of modules 204, each equipped with bases 202, and fixed at a small angle α with respect to each other. The bases may be "U-beams" that are adhesively coupled together. Each module 204 includes a substrate 204A and a closure 204B with a thin film portion, commonly referred to as a "gap" in which the readers and/or writers 206 are formed. In use, a tape 208 is moved over the modules 204 along a media (tape) bearing surface 209 in the manner shown for reading and writing data on the tape 208 using the readers and writers. The wrap angle θ of the tape 208 at edges going onto and exiting the flat media support surfaces 209 are usually between about 0.1 degree and about 5 degrees.

The substrates 204A are typically constructed of a wear resistant material, such as a ceramic. The closures 204B made of the same or similar ceramic as the substrates 204A.

The readers and writers may be arranged in a piggyback or merged configuration. An illustrative piggybacked configuration comprises a (magnetically inductive) writer transducer on top of (or below) a (magnetically shielded) reader transducer (e.g., a magnetoresistive reader, etc.), wherein the poles of the writer and the shields of the reader are generally separated. An illustrative merged configuration comprises one reader shield in the same physical layer as one writer pole (hence, "merged"). The readers and writers may also be arranged in an interleaved configuration. Alternatively, each array of channels may be readers or writers only. Any of these arrays may contain one or more servo track readers for reading servo data on the medium.

Figure 2A:
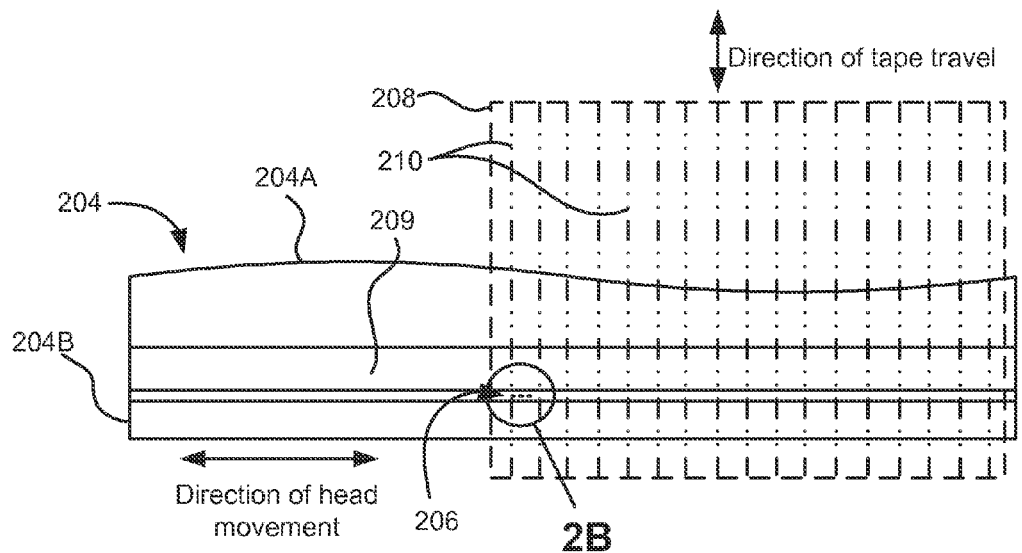
FIG. 2A is a tape bearing surface view taken from Line 2A of FIG. 2.

FIG. 2A illustrates the tape bearing surface 209 of one of the modules 204 taken from Line 2A of FIG. 2. A representative tape 208 is shown in dashed lines. The module 204 is preferably long enough to be able to support the tape as the head steps between data bands.

In this example, the tape 208 includes 4 to 22 data bands, e.g., with 16 data bands and 17 servo tracks 210, as shown in FIG. 2A on a one-half inch wide tape 208. The data bands are defined between servo tracks 210. Each data band may include a number of data tracks, for example 512 data tracks (not shown). During read/write operations, the readers and/or writers 206 are positioned to specific track positions within one of the data bands. Outer readers, sometimes called servo readers, read the servo tracks 210. The servo signals are in turn used to keep the readers and/or writers 206 aligned with a particular set of tracks during the read/write operations.

Figure 2B:
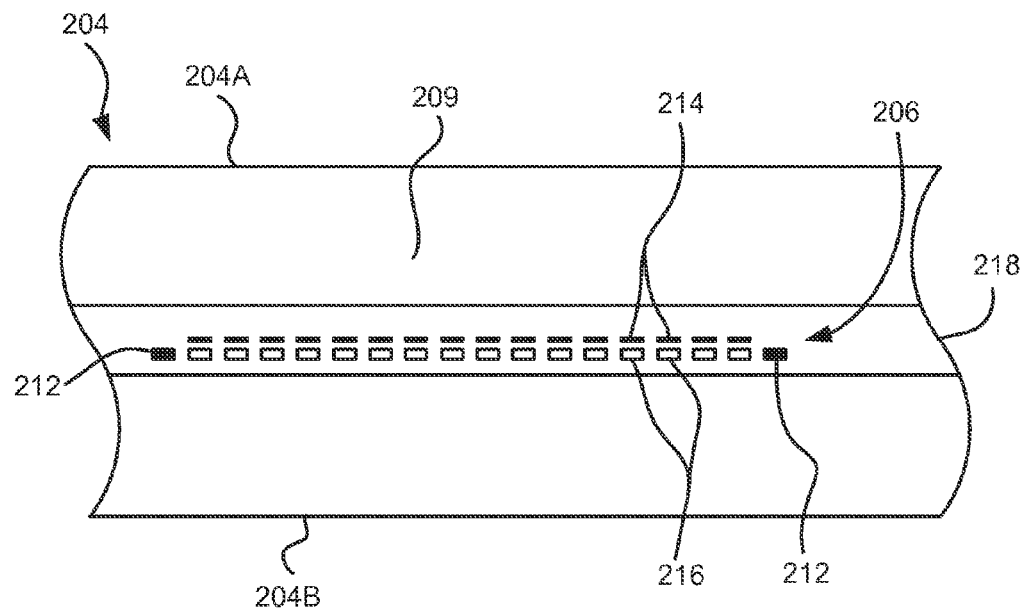
FIG. 2B is a detailed view taken from Circle 2B of FIG. 2A.

FIG. 2B depicts a plurality of readers and/or writers 206 formed in a gap 218 on the module 204 in Circle 2B of FIG. 2A. As shown, the array of readers and writers 206 includes, for example, 16 writers 214, 16 readers 216 and two servo readers 212, though the number of elements may vary. Illustrative embodiments include 8, 16, 32, 40, and 64 readers and/or writers 206 per array. A preferred embodiment includes 32 readers per array and/or 32 writers per array, where the actual number of transducing elements could be greater, e.g., 33, 34, etc. This allows the tape to travel more slowly, thereby reducing speed-induced tracking and mechanical difficulties and/or execute fewer "wraps" to fill or read the tape. While the readers and writers may be arranged in a piggyback configuration as shown in FIG. 2B, the readers 216 and writers 214 may also be arranged in an interleaved configuration. Alternatively, each array of readers and/or writers 206 may be readers or writers only, and the arrays may contain one or more servo readers 212. As noted by considering FIGS. 2 and 2A-B together, each module 204 may include a complementary set of readers and/or writers 206 for such things as bi-directional reading and writing, read-while-write capability, backward compatibility, etc.

Figure 2C:
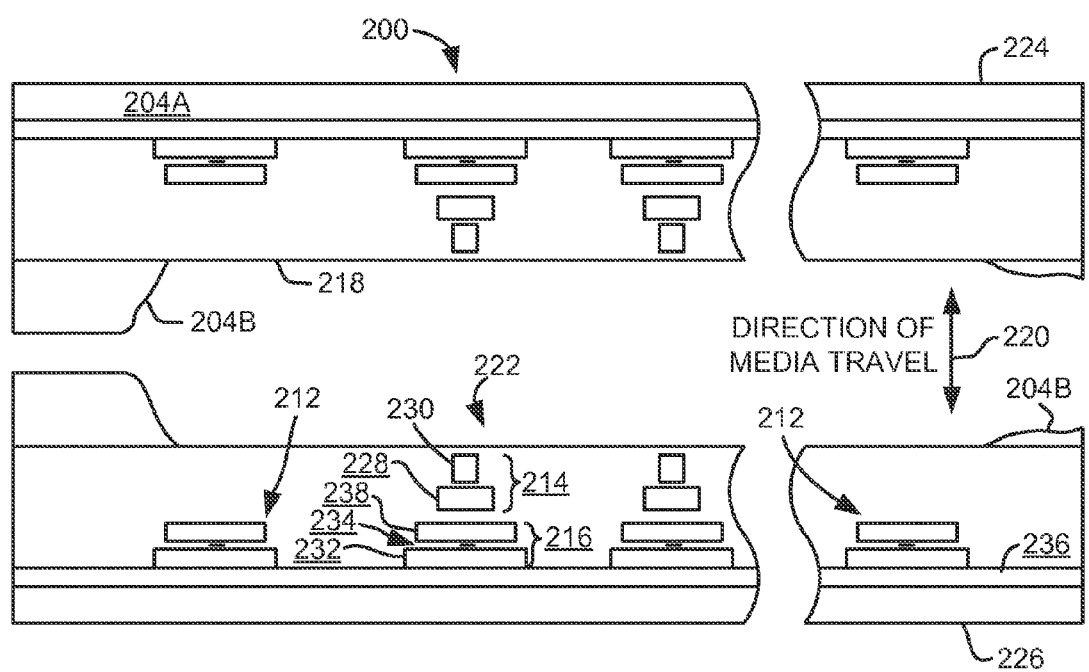
FIG. 2C is a detailed view of a partial tape bearing surface of a pair of modules.

FIG. 2C shows a partial tape bearing surface view of complimentary modules of a magnetic tape head 200 according to one embodiment. In this embodiment, each module has a plurality of read/write (R/W) pairs in a piggyback configuration formed on a common substrate 204A and an optional electrically insulative layer 236. The writers, exemplified by the write head 214 and the readers, exemplified by the read head 216, are aligned parallel to a direction of travel of a tape medium thereacross to form an R/W pair, exemplified by the R/W pair 222.

Several R/W pairs 222 may be present, such as 8, 16, 32 pairs, etc. The R/W pairs 222 as shown are linearly aligned in a direction generally perpendicular to a direction of tape travel thereacross. However, the pairs may also be aligned diagonally, etc. Servo readers 212 are positioned on the outside of the array of R/W pairs, the function of which is well known.

Generally, the magnetic tape medium moves in either a forward or reverse direction as indicated by arrow 220. The magnetic tape medium and head assembly 200 operate in a transducing relationship in the manner well-known in the art. The piggybacked MR head assembly 200 includes two thin-film modules 224 and 226 of generally identical construction.

Modules 224 and 226 are joined together with a space present between closures 204B thereof (partially shown) to form a single physical unit to provide read-while-write capability by activating the writer of the leading module and reader of the trailing module aligned with the writer of the leading module parallel to the direction of tape travel relative thereto. When a module 224, 226 of a piggyback head 200 is constructed, layers are formed in the gap 218 created above an electrically conductive substrate 204A (partially shown), e.g., of AlTiC, in generally the following order for the R/W pairs 222: an insulating layer 236, a first shield 232 typically of an iron alloy such as NiFe (permalloy), CZT or Al—Fe—Si (Sendust), a sensor 234 for sensing a data track on a magnetic medium, a second shield 238 typically of a nickel-iron alloy (e.g., 80/20 Permalloy), first and second writer pole tips 228, 230, and a coil (not shown).

The first and second writer poles 228, 230 may be fabricated from high magnetic moment materials such as 45/55 NiFe. Note that these materials are provided by way of example only, and other materials may be used. Additional layers such as insulation between the shields and/or pole tips and an insulation layer surrounding the sensor may be present. Illustrative materials for the insulation include alumina and other oxides, insulative polymers, etc.

Each drive product has different generations and each generation typically results in creation of a newly formulated tape that is usually smoother, less abrasive and has denser magnetic particle packing than the previous generation.

The current method employed by media vendors to gauge tape abrasivity involves running tape over the tip of a triangular shaped AlFeSil wear bar. This method has been shown to be not representative of actual head wear, and not a good gauge of tape abrasivity.

According to a preferred embodiment, a testing system and/or methodology may be used for gauging media abrasivity relative to particular types of modules. Various approaches disclosed herein more accurately measure media abrasivity and/or are more representative of the head wear observed in actual product usage, in addition to being fast, accurate, and easy to use.

Figure 3:
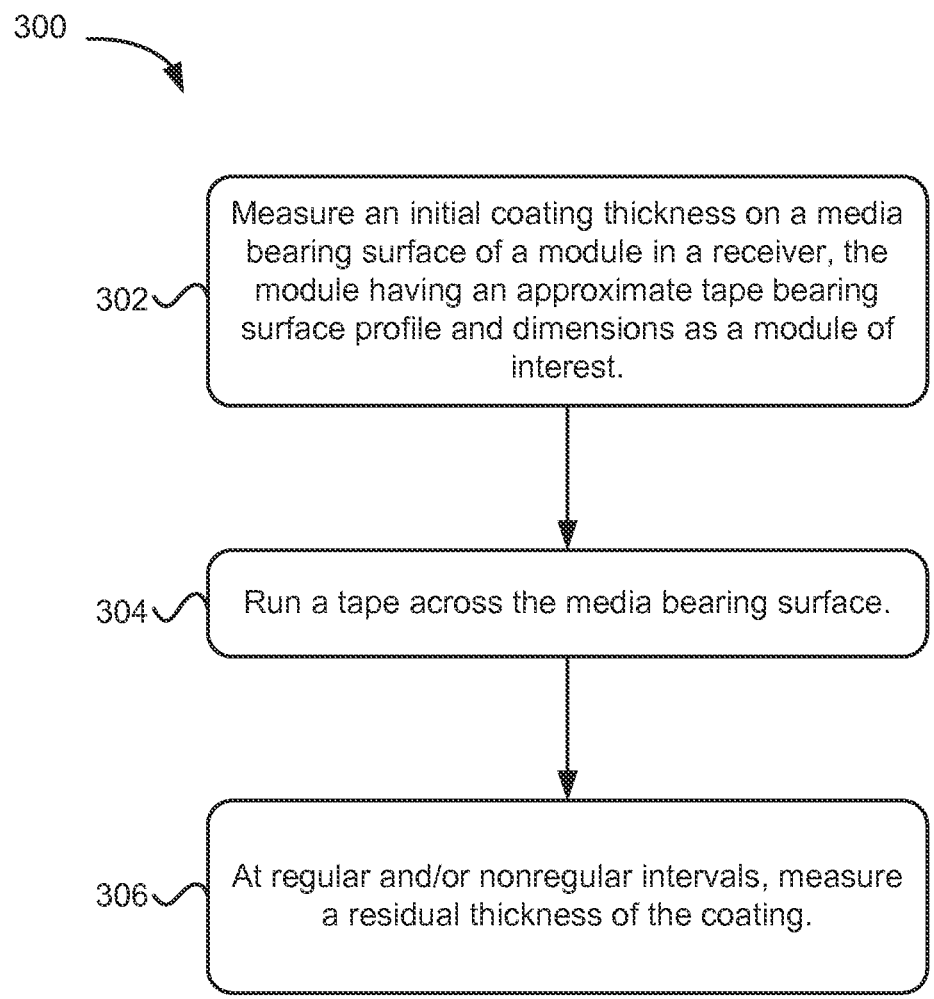
FIG. 3 depicts a method according to one embodiment.

Now referring to FIG. 3, a method 300 includes measuring an initial coating thickness on a tape bearing surface of a module in a carrier, the module having an approximate tape bearing surface profile and dimensions as a module of interest. See operation 302. Illustrative devices for performing the measuring are described below.

In a preferred approach, a "module of interest" may be any functional module that is in production, may go into production, or simply has a shape similar to a module that will be used in a product.

In one embodiment, a module that may be used in the testing may include a body having a tape bearing surface. In a preferred approach, the body may have an approximate tape bearing surface profile and dimensions as a module of interest. In another approach, the module may be an operative module for a tape head according to any of the embodiments described and/or suggested herein, e.g., one of the modules of interest. In one particular approach, the module may additionally include a coating on the tape bearing surface.

Moreover, a module that looks like a tape head, but without any of the recording elements may be used to reduce the production time and cost of the testing platform. Thus, in one approach, the module may be nonfunctional, as in a case where the module may be a dummy module, a replica, a defective real module, etc.

In various approaches of method 300, the module may incorporate any of the modules mentioned and/or suggested herein. In another approach, the module may be part of a completed head assembly according to any of the embodiments described and/or suggested herein. In one approach, the head assembly may be received in the carrier.

In various approaches, the carrier may include plastic, glass, ceramic, metal, etc. or any other material which would be apparent to one skilled in the art upon reading the present description. Moreover, the carrier may include a coupling mechanism such as a slot, clamp, etc. for coupling the module to the carrier.

With continued reference to FIG. 3, the method 300 additionally includes running a tape across the tape bearing surface of the module. See operation 304. According to various approaches, the tape may include a newly formulated tape, a tape from a previous generation, a tape selected from a bank of tapes, etc.

In operation 306, a residual thickness of the coating is measured at regular and/or nonregular intervals. For example, the tape may be run for a short period, and then a coating wear measurement may be taken, followed by running the tape again for a second period and re-measuring, and so on. In one approach, an initial coating thickness may be taken before the tape is run across the coating to be used as a baseline when comparing later coating wear measurements.

In one approach, the measuring may be performed using any of the measuring devices mentioned and/or suggested herein. According to another approach, the module may be removed from the carrier for the conducting the measuring.

Referring now to FIG. 4A, a system 400 includes a carrier 402 which may be for receiving a module 204. The system 400 additionally includes a transport mechanism 404 which may be for running a tape 406 across a tape bearing surface 209 of the module 204.

The module has a coating 414 thereon that wears when the tape is run thereacross due to atmospheric pressure forcing the tape against the subambient interface between the module and the tape. The corners of the module serve to skive air from the tape to create the subambient condition. See also coating 414 of FIGS. 6B and 7B. An extent of the wear of the coating is indicative of the expected wear of the module of interest.

During tape wear testing, the tape is run across the module, and an extent of wear of the coating is measured. Illustrative methods for performing the coating measurements are described herein.

With continued reference to FIG. 4A, the system 400 additionally includes a measuring device 412 for measuring an extent of wear of the coating 414 on the tape bearing surface 209 of the module 204.

In accordance with various approaches, the measuring device 412 may include an ellipsometer, a stylus profiler, etc. or any other measuring device which would be apparent to one skilled in the art upon reading the present description. In a preferred approach, the measuring device is an ellipsometer, as the measurements made by it are fast, accurate and do not disturb and/or contact the tape bearing surface. One approach implements an ex-situ ellipsometer where the module is removed from the tester for measurements. However, in particularly preferred approaches, an in-situ configuration may be employed so that coating thickness measurements can be captured through automation in a single tool.

Transparent or substantially transparent coatings are preferably used with embodiments which utilize an ellipsometer. According to various approaches, the coating may include Diamond Like Carbon (DLC), glass, metal oxides such as alumina, chrome oxide, etc., nitrides, polycrystalline alumina, etc. or any other transparent, substantially transparent and/or semi-transparent coating which would be apparent to one skilled in the art upon reading the present description. However, in various other embodiments which do not incorporate an ellipsometer, a non-transparent or substantially non-transparent coating may be used in regions where the thickness is measured.

In approaches which include alumina in the coating, it is preferable that the alumina be deposited in a manner so that it grows in a crystalline, polycrystalline, or semi-crystalline fashion thereby preventing the tape from wearing off the coating layer too quickly. In a particularly preferred approach, the coating is primarily e.g., at least 80% up to 100%, polycrystalline alumina.

For the wear measurements to be accurate and meaningful, a coating with appropriate hardness may preferably be selected such that the difference in tape abrasivity can be easily discerned within a relatively short period of time. In one approach, the coating may preferably have a similar coefficient of friction as the module of interest such that stiction and friction do not harm the system. This coating material may be applied to various heads, including, but not limited to contoured heads to gauge tape abrasivity in different head structures and profiles.

In a preferred approach, the coating may have a deposition thickness of at least about 10 nanometers, more preferably from about 50 nanometers to about 200 nanometers, but may be higher or lower in various embodiments.

Figure 4B:
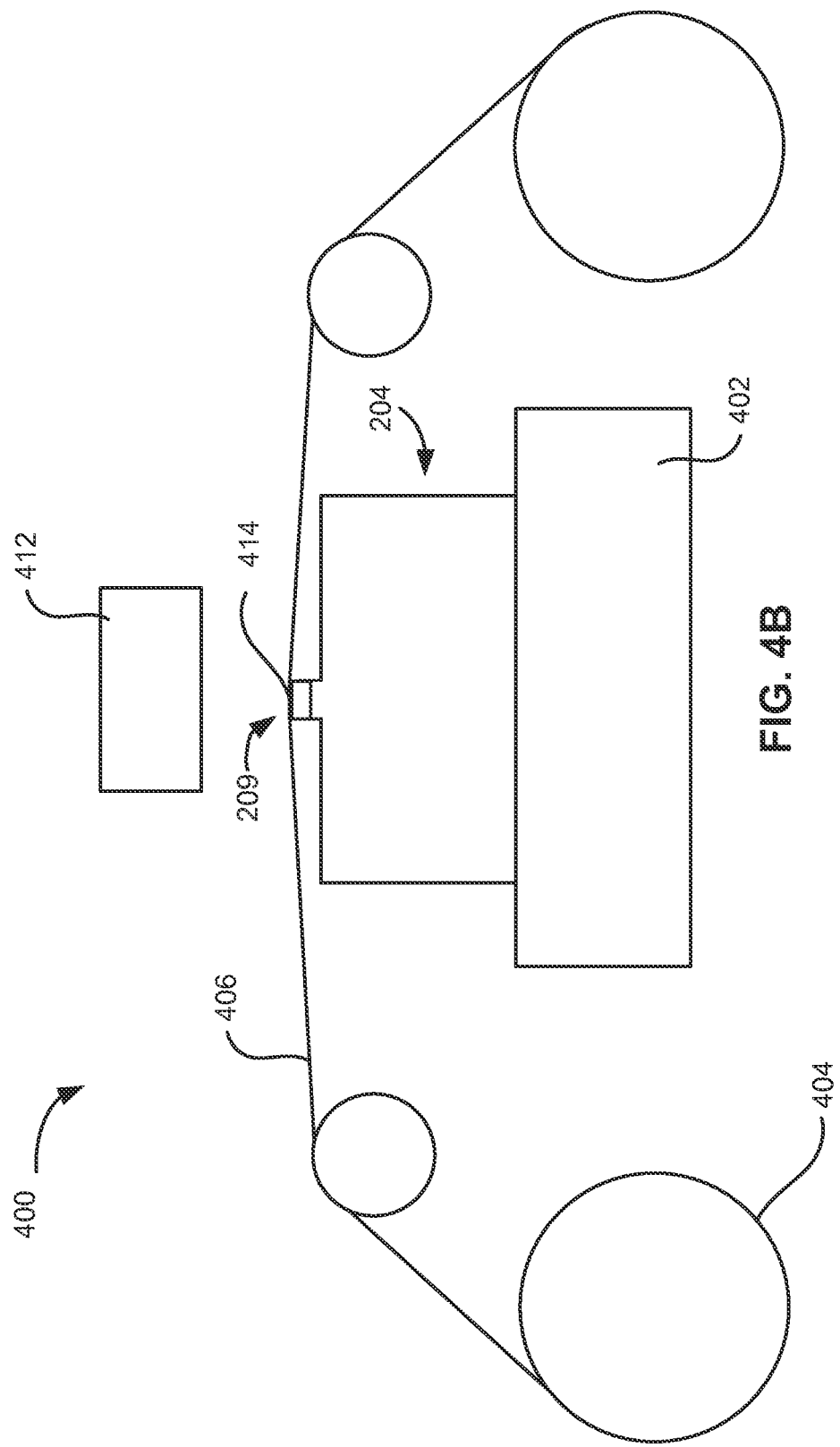
FIG. 4B is a partial cross-sectional view of a tape head according to one embodiment.

In a variation depicted in FIG. 4B, the module 204 has a narrower tape bearing surface as measured in a direction of tape travel thereacross. An illustrative width in the direction of tape travel may be approximately comparable to a width of the tape tents formed at the corners of the tape bearing surface. After the tape runs for a while, the coating evolves into a stable cylindrical contour, at which point an additional tape contact pressure term is T/RW, where T is tape tension, R is the radius of the contour, and W is the width of the tape. The coating 414 is thicker than in the previous approach, e.g., between about 500 nm to about 5 microns. This embodiment is useful for evaluating wear resistance of thicker and/or harder coatings.

Figure 5:
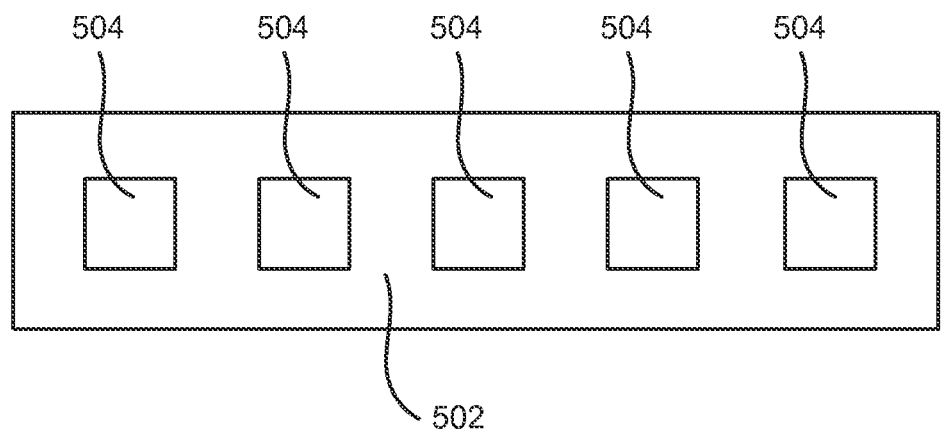
FIG. 5 is a top-down view of a coating scheme according to one embodiment.

Now referring to the top down view of a head depicted in FIG. 5, according to one illustrative embodiment, the coating may include a bulk material 502 and one or more sections of a second material 504 at predetermined positions relative to the bulk material 502. Preferably, the bulk and second materials are different. In one approach, the second material 504 may include aluminum-iron-silicon (AlFeSil), Sendust, etc. In another approach, the bulk material 502 may include, but is not limited to alumina or any other suitable material described or alluded to herein. The sections of second material may have any shape, and may be arranged in any manner. The design depicted in FIG. 5 allows for the possibility of differential wear which may allow for different sections of the coating to wear down at different rates. Moreover, this differential wear may provide additional information as to the wear rates of different materials applied in different testing schemes.

Referring back to FIG. 4, in one approach, the measuring device 412 may be configured to use areas of the tape bearing surface 209 not contacted by the tape 406 as reference gauges for the measuring. In another approach, the carrier 402 and measuring device 412 may be configured and/or positioned to allow measuring the extent of wear of the coating 414 without removing the module 204 from the carrier 402.

Figure 6A:
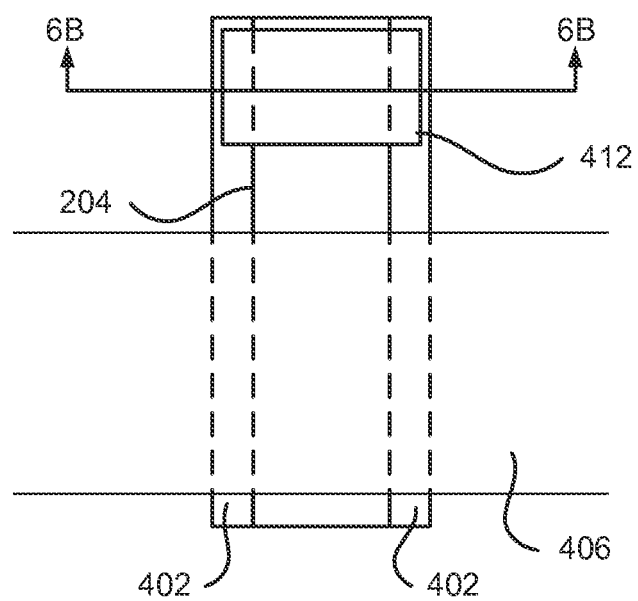
FIG. 6A is a partial top-down view of a coating thickness measuring device according to one embodiment.
Figure 6B:
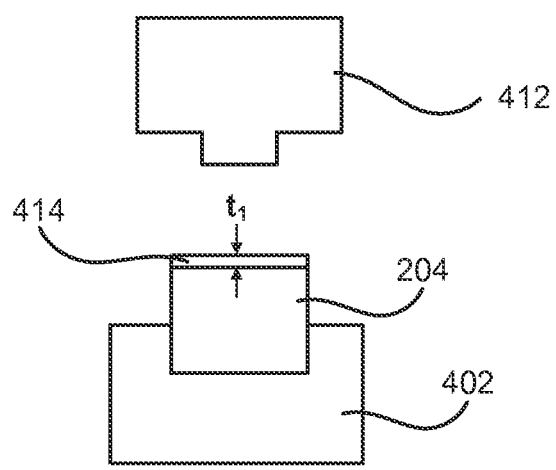
FIG. 6B is a partial cross-sectional view of a coating thickness measuring device according to one embodiment.

As depicted in the cross-sectional and top down views of FIGS. 6A-6B respectively, optionally after the initial (control) thickness $t_1$ is measured by the measuring device 412, the module 204 is positioned below the tape 406, and/or the tape is positioned over the module, and the tape is run across the module 204 to induce wear.

Figure 7A:
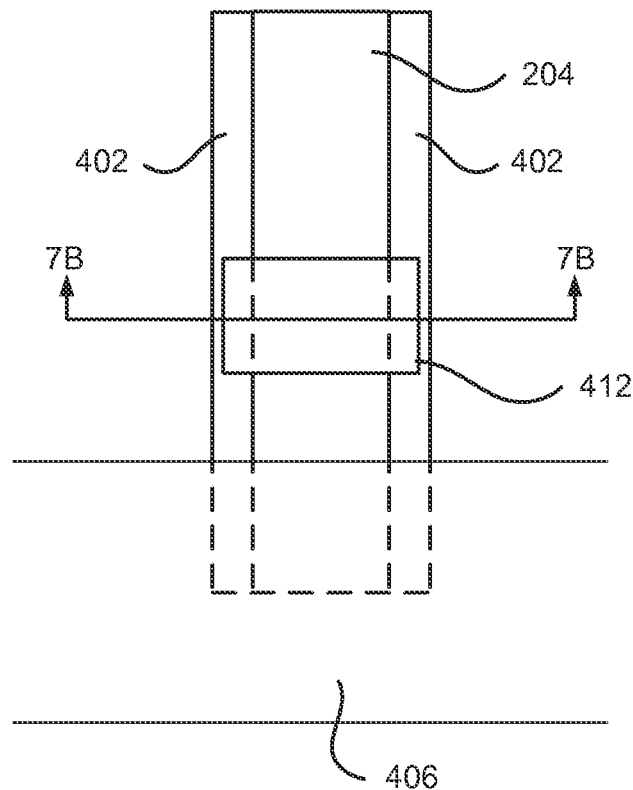
FIG. 7A is a partial top-down view of a coating thickness measuring device according to one embodiment.
Figure 7B:
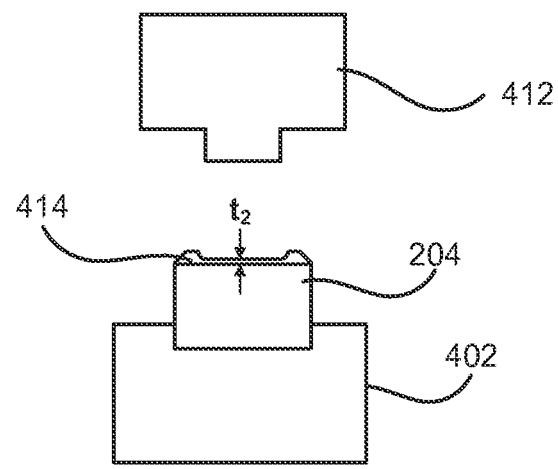
FIG. 7B is a partial cross-sectional view of a coating thickness measuring device according to one embodiment.

According to one embodiment as depicted in the cross-sectional and top down views of FIGS. 7A-7B, respectively, measuring the residual thickness $t_2$ of the coating may include, e.g., at regular and/or nonregular intervals, creating a relative movement between the measuring device 412 and the module 204 (e.g., via the carrier 402) on that a portion or all of the coating 414 previously below the running tape 406 becomes exposed. Then, the measuring device 412, such as an ellipsometer, may measure the thickness $t_2$ of the coating 414 in a region where the tape 406 has run thereacross. It is preferable that this residual thickness is measured near the center of the coating as measured in a direction of tape travel, because the coating near the corners of the head may exhibit a wear pattern resulting from tape tenting (as seen in FIG. 7B), and thus would give inaccurate readings if used as the residual thickness.

After the residual thickness is measured, the module 204 and carrier 402 and/or tape 406 may be positioned in the operating arrangement and the tape run over the module again. This process may be repeated several times.

To determine the extent of wear, the measuring device 412 may measure the control thickness $t_1$ of the coating 414 in an area which never comes into contact with tape 406, which is used as the control thickness for comparison to the residual thickness measurement(s). This allows for an accurate comparison between the control thickness $t_1$ and the residual thickness $t_2$ without having to unwind the head each time a coating wear measurement is made. In an alternate approach, noted above, the initial thickness may be measured prior to running the tape.

In further embodiments, the testing system may be operated with opposing modules, single modules, triple modules, etc.

Depending on the abrasivity of the tape media, the coating may wear at different rates. According to the embodiments described herein, measurements of the coating thickness on a module having a shape like the module of interest reveal how quickly a certain tape media may be wearing the coating. These measurements are directly related to media abrasivity and how quickly the media will wear a given module of interest while subjected to actual product usage.

According to one approach, the wear test, according to any of the embodiments described herein, may be conducted on any newly developed coating, e.g., to compare the characteristics of the coating with some standard or threshold of tape head wear to evaluate the particular coating's configuration.

Additionally, optical and/or stylus profile measurements may be taken at the end of the test to capture the overall head profile created by the tape.

It will be clear that the various features of the foregoing methodologies may be combined in any way, creating a plurality of combinations from the descriptions presented above.

It will also be clear to one skilled in the art that the methodology of the present invention may suitably be embodied in a logic apparatus comprising logic to perform various steps of the methodology presented herein, and that such logic may comprise hardware components or firmware components.

It will be equally clear to one skilled in the art that the logic arrangement in various approaches may suitably be embodied in a logic apparatus comprising logic to perform various steps of the method, and that such logic may comprise components such as logic gates in, for example, a programmable logic array. Such a logic arrangement may further be embodied in enabling means or components for temporarily or permanently establishing logical structures in such an array using, for example, a virtual hardware descriptor language, which may be stored using fixed or transmittable carrier media.

It will be appreciated that the methodology described above may also suitably be carried out fully or partially in software running on one or more processors (not shown), and that the software may be provided as a computer program element carried on any suitable data carrier (also not shown) such as a magnetic or optical computer disc. The channels for the transmission of data likewise may include storage media of all descriptions as well as signal carrying media, such as wired or wireless signal media.

Embodiments of the present invention may suitably be embodied as a computer program product for use with a computer system. Such an implementation may comprise a series of computer readable instructions either fixed on a tangible medium, such as a computer readable medium, for example, diskette, CD-ROM, ROM, or hard disk, or transmittable to a computer system, via a modem or other interface device, over either a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic, or optical, or transmitted using any communications technology, present or future, including but not limited to optical, infrared, or microwave. It is contemplated that such a computer program product may be distributed as a removable medium with accompanying printed or electronic documentation, for example, shrink-wrapped software, preloaded with a computer system, for example, on a system ROM or fixed disk, or distributed from a server or electronic bulletin board over a network, for example, the Internet or World Wide Web.

Communications components such as input/output or I/O devices (including but not limited to keyboards, displays, pointing devices, etc.) can be coupled to the system either directly or through intervening I/O controllers.

Communications components such as buses, interfaces, network adapters, etc. may also be coupled to the system to enable the data processing system, e.g., host, to become coupled to other data processing systems or remote printers or storage devices through intervening private or public networks. Modems, cable modem and Ethernet cards are just a few of the currently available types of network adapters.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A method, comprising:
   measuring an initial coating thickness on a tape bearing surface of a module in a carrier;
   running a tape across the tape bearing surface; and
   at a plurality of regular temporal intervals, measuring a residual thickness of the coating.

2. A method as recited in claim 1, wherein the module is part of a completed head assembly, the head assembly being received in the carrier.

3. A method as recited in claim 1, wherein the module is an operative module for a tape head.

4. A method as recited in claim 1, wherein the module is nonfunctional, wherein the measuring is performed using an ellipsometer, wherein the coating is transparent.

5. A method as recited in claim 1, wherein the measuring is performed using an ellipsometer.

6. A method as recited in claim 1, further comprising taking stylus profile measurements.

7. A method as recited in claim 1, further comprising, after running the tape across the tape bearing surface, using areas of the tape bearing surface not contacted by the tape as reference gauges for the measuring.

8. A method as recited in claim 1, wherein the coating has a similar coefficient of friction as a module of interest.

9. A method as recited in claim 8, wherein the module of interest is a functional module that is concurrently in production for use in a product.

10. A method as recited in claim 1, wherein the coating has a deposition thickness of at least about 10 nanometers.

11. A method as recited in claim 1, wherein the coating is transparent.

12. A method as recited in claim 1, wherein the coating is primarily polycrystalline alumina.

13. A method as recited in claim 1, wherein the initial coating thickness is measured in an area of the tape bearing surface not contacted by the tape, after running the tape across the tape bearing surface.

14. A method, comprising:
    measuring an initial coating thickness on a tape bearing surface of a module in a carrier;
    running a tape across the tape bearing surface; and
    at a plurality of regular intervals, measuring a residual thickness of the coating,
    wherein the coating includes a bulk material and one or more sections of a second material at predetermined positions relative to the bulk material.

15. A method as recited in claim 14, wherein the one or more sections of the second material have defined shapes at a tape bearing surface of the coating.

16. A method as recited in claim 14, wherein at least one of the sections of the second material has a rectangular shape along a tape bearing surface of the coating, the at least one of the sections being surrounded by the bulk material along the tape bearing surface of the coating.

17. A method as recited in claim 14, wherein the second material is formed above the tape bearing surface of the module and has a different chemical composition than the bulk material.

18. A method as recited in claim 14, wherein the second material is constructed of a material selected from a group consisting of AlFeSil and Sendust.

19. A method as recited in claim 14, wherein the module is nonfunctional, wherein the measuring is performed using an ellipsometer, wherein the coating is transparent.

20. A method as recited in claim 14, wherein the initial coating thickness is measured in an area of the tape bearing surface not contacted by the tape, after running the tape across the tape bearing surface.

* * * * *